US012762329B2

(12) United States Patent
Hasegawa

(10) Patent No.: US 12,762,329 B2
(45) Date of Patent: Oct. 13, 2026

(54) INFORMATION PROCESSING APPARATUS, INFORMATION PROCESSING METHOD, AND INFORMATION PROCESSING PROGRAM

(71) Applicant: FUJIFILM CORPORATION, Tokyo (JP)

(72) Inventor: Yu Hasegawa, Tokyo (JP)

(73) Assignee: FUJIFILM CORPORATION, Tokyo (JP)

( * ) Notice: Subject to any disclaimer, the term of this patent is extended or adjusted under 35 U.S.C. 154(b) by 125 days.

(21) Appl. No.: 18/805,547

(22) Filed: Aug. 15, 2024

(65) Prior Publication Data

US 2024/0403544 A1 Dec. 5, 2024

Related U.S. Application Data

(63) Continuation of application No. PCT/JP2023/005844, filed on Feb. 17, 2023.

(30) Foreign Application Priority Data

Feb. 18, 2022 (JP) ................................ 2022-024251

(51) Int. Cl.
*G06F 40/169* (2020.01)
*G16H 30/40* (2018.01)

(52) U.S. Cl.
CPC .......... *G06F 40/169* (2020.01); *G16H 30/40* (2018.01)

(58) Field of Classification Search
None
See application file for complete search history.

(56) References Cited

U.S. PATENT DOCUMENTS

2019/0267120 A1 8/2019 Hirakawa
2019/0279751 A1 9/2019 Nakamura et al.

FOREIGN PATENT DOCUMENTS

| | | | | |
|---|---|---|---|---|
| JP | 2003-108664 | A | | 4/2003 |
| JP | 2004265039 | A | * | 9/2004 |
| JP | 4125439 | B2 | * | 7/2008 |
| JP | 2019-008817 | A | | 1/2009 |
| JP | 2009-238038 | A | | 10/2009 |
| JP | 2009-238039 | A | | 10/2009 |
| JP | 2012-053632 | A | | 3/2012 |
| JP | 2019-149005 | A | | 9/2019 |
| JP | 2019-153250 | A | | 9/2019 |

OTHER PUBLICATIONS

International Search Report issued in International Application No. PCT/JP2023/005844 on May 16, 2023.
Written Opinion of the ISA issued in International Application No. PCT/JP2023/005844 on May 16, 2023.

* cited by examiner

*Primary Examiner* — Quynh H Nguyen
(74) *Attorney, Agent, or Firm* — SOLARIS Intellectual Property Group, PLLC

(57) ABSTRACT

An information processing apparatus including at least one processor, wherein the processor is configured to: acquire at least one existing sentence and a new sentence described after the existing sentence, mutually different medical information of the same subject being described in the existing sentence and the new sentence; and determine an arrangement order of the existing sentence and the new sentence in accordance with a predetermined rule based on the medical information described in each of the existing sentence and the new sentence.

16 Claims, 8 Drawing Sheets

INFORMATION PROCESSING APPARATUS, INFORMATION PROCESSING METHOD, AND INFORMATION PROCESSING PROGRAM

CROSS REFERENCE TO RELATED APPLICATIONS

This application is a continuation of International Application No. PCT/JP2023/005844, filed on Feb. 17, 2023, which claims priority from Japanese Patent Application No. 2022-024251, filed on Feb. 18, 2022. The entire disclosure of each of the above applications is incorporated herein by reference.

BACKGROUND

Technical Field

The present disclosure relates to an information processing apparatus, an information processing method, and an information processing program.

Related Art

In the related art, image diagnosis is performed using medical images obtained by imaging apparatuses such as computed tomography (CT) apparatuses and magnetic resonance imaging (MRI) apparatuses. Further, medical images are analyzed via computer aided detection/diagnosis (CAD) using a discriminator in which learning is performed by deep learning or the like, and regions of interest including structures, lesions, and the like included in the medical images are detected and/or diagnosed. The medical images and analysis results via CAD are transmitted to a terminal of a healthcare professional such as a radiologist who interprets the medical images. The healthcare professional such as a radiologist interprets the medical image by referring to the medical image and analysis result using his or her own terminal and creates an interpretation report.

In addition, various methods have been proposed to support the creation of interpretation reports in order to reduce the burden of the interpretation work of a radiologist. For example, JP2019-153250A discloses a technology for creating an interpretation report based on a keyword input by a radiologist and an analysis result of a medical image. In the technology disclosed in JP2019-153250A, a sentence to be included in the interpretation report is created by using a recurrent neural network trained to generate a sentence from input characters.

For example, JP2019-149005A discloses that, in a case in which character information representing finding content for a medical image is input, medical information including an analysis result of the medical image is referred to, content candidates related to the character information are presented, and a medical document is created into which content selected from among the content candidates is inserted.

Incidentally, an interpretation report may include a plurality of comments on findings that differ in content, such as an organ to be described, a lesion, and an imaging date and time. For ease of reading, it is desirable to consider the description order of a plurality of comments on findings included in an interpretation report, and to describe comments on findings with similar contents together. However, in the technique of the related art, the description order of comments on findings is not considered, and thus an interpretation report that is difficult to read may be created.

SUMMARY

The present disclosure provides an information processing apparatus, an information processing method, and an information processing program that can support creation of an interpretation report.

According to a first aspect of the present disclosure, there is provided an information processing apparatus comprising at least one processor, in which the processor is configured to: acquire at least one existing sentence and a new sentence described after the existing sentence, mutually different medical information of the same subject being described in the existing sentence and the new sentence; and determine an arrangement order of the existing sentence and the new sentence in accordance with a predetermined rule based on the medical information described in each of the existing sentence and the new sentence.

According to a second aspect of the present disclosure, in the first aspect, the processor may be configured to specify the medical information from each of the existing sentence and the new sentence.

According to a third aspect of the present disclosure, in the first or second aspect, the processor may be configured to determine, in a case in which there are a plurality of the existing sentences, the arrangement order including rearrangement of the existing sentences.

According to a fourth aspect of the present disclosure, in the first or second aspect, the processor may be configured to determine, in a case in which there are a plurality of the existing sentences, the arrangement order for determining an insertion position of the new sentence while an arrangement order of the plurality of existing sentences is fixed.

According to a fifth aspect of the present disclosure, in any one of the first to fourth aspects, the medical information may indicate at least one of a type of an organ, a type of a lesion, or a type of an examination, and the processor may be configured to determine the arrangement order such that the existing sentence and the new sentence are arranged for each type of the medical information.

According to a sixth aspect of the present disclosure, in any one of the first to fifth aspects, the medical information may indicate a property of a lesion, and the processor may be configured to determine the arrangement order such that the existing sentence and the new sentence are arranged for each property of the medical information.

According to a seventh aspect of the present disclosure, in any one of the first to sixth aspects, the processor may be configured to: specify a factuality regarding the medical information from each of the existing sentence and the new sentence; and determine the arrangement order such that the existing sentence and the new sentence are arranged for each factuality regarding the medical information.

According to an eighth aspect of the present disclosure, in any one of the first to seventh aspects, the medical information may have a predetermined importance, and the processor may be configured to determine the arrangement order such that the existing sentence and the new sentence with a higher importance of the medical information are positioned closer to a beginning of a sentence.

According to a ninth aspect of the present disclosure, in any one of the first to eighth aspects, the medical information may indicate a point in time at which an examination is performed, and the processor may be configured to determine the arrangement order such that the existing sentence and the new sentence are arranged in chronological order.

According to a tenth aspect of the present disclosure, in any one of the first to ninth aspects, the processor may be configured to: acquire a past document including a sentence describing medical information of the subject; and determine the arrangement order based on whether or not the medical information corresponding to the existing sentence and the new sentence is included in the past document.

According to an eleventh aspect of the present disclosure, in any one of the first to tenth aspects, at least one of the existing sentence or the new sentence may include a sentence generated based on a medical image.

According to a twelfth aspect of the present disclosure, in any one of the first to eleventh aspects, the processor may be configured to rearrange the existing sentence and the new sentence based on the determined arrangement order.

According to a thirteenth aspect of the present disclosure, in the twelfth aspect, the processor may be configured to highlight the new sentence and display the existing sentence and the new sentence after the rearrangement on a display.

According to a fourteenth aspect of the present disclosure, in the twelfth or thirteenth aspect, the processor may be configured to highlight, in a case in which the existing sentence is rearranged, the rearranged existing sentence and display the existing sentence and the new sentence after the rearrangement on a display.

According to a fifteenth aspect of the present disclosure, in any one of the first to fourteenth aspects, the processor may be configured to display information indicating a rule for the arrangement order on a display.

According to a sixteenth aspect of the present disclosure, there is provided an information processing method comprising: acquiring at least one existing sentence and a new sentence described after the existing sentence, mutually different medical information of the same subject being described in the existing sentence and the new sentence; and determining an arrangement order of the existing sentence and the new sentence in accordance with a predetermined rule based on the medical information described in each of the existing sentence and the new sentence.

According to a seventeenth aspect of the present disclosure, there is provided an information processing program for causing a computer to execute a process comprising: acquiring at least one existing sentence and a new sentence described after the existing sentence, mutually different medical information of the same subject being described in the existing sentence and the new sentence; and determining an arrangement order of the existing sentence and the new sentence in accordance with a predetermined rule based on the medical information described in each of the existing sentence and the new sentence.

The information processing apparatus, the information processing method, and the information processing program according to the aspects of the present disclosure can support creation of an interpretation report.

DETAILED DESCRIPTION

Figure 1:
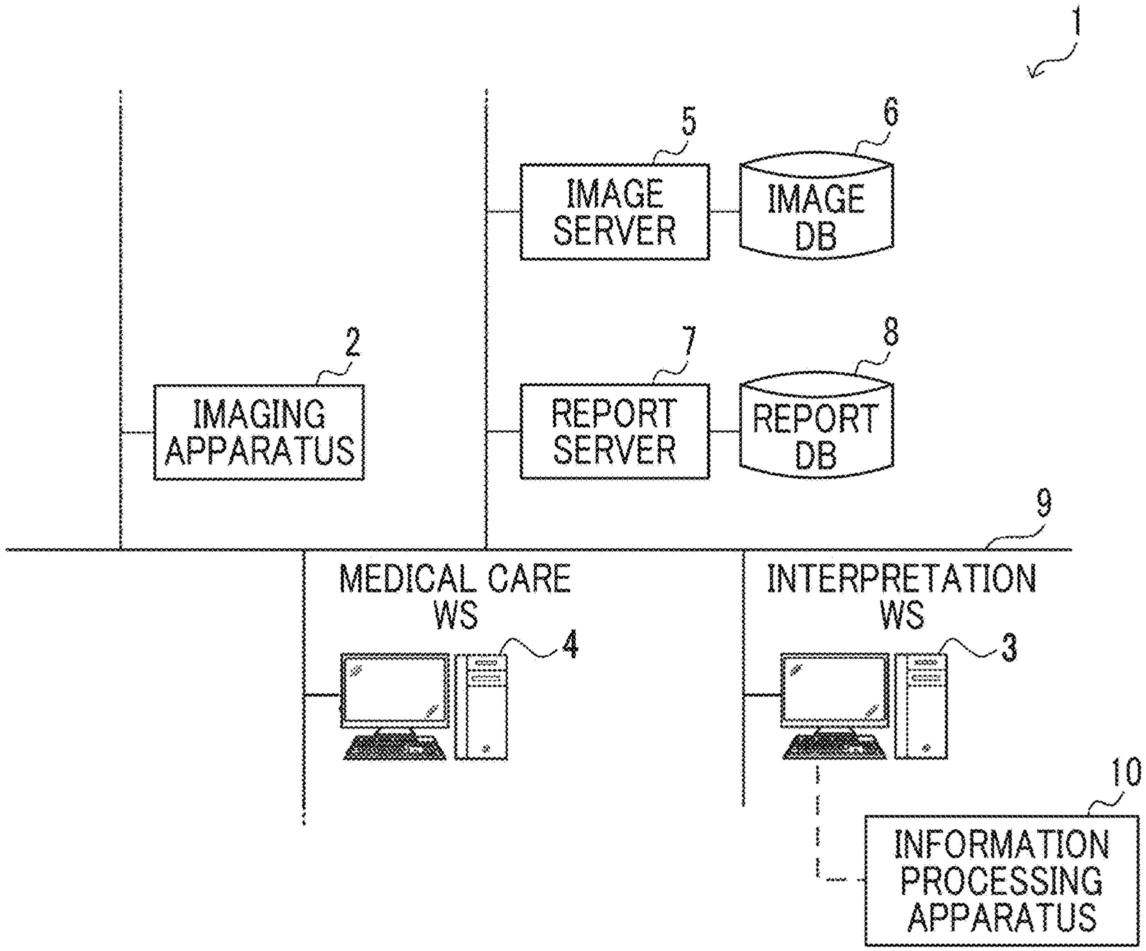
FIG. 1 is a diagram showing an example of a schematic configuration of an information processing system.

Hereinafter, embodiments of the present disclosure will be described with reference to the drawings. First, a configuration of an information processing system 1 to which an information processing apparatus of the present disclosure is applied will be described. FIG. 1 is a diagram showing a schematic configuration of the information processing system 1. The information processing system 1 shown in FIG. 1 performs imaging of an examination target part of a subject and storing of a medical image acquired by the imaging based on an examination order from a doctor in a medical department using a known ordering system. In addition, the information processing system 1 performs an interpretation work of a medical image and creation of an interpretation report by a radiologist and viewing of the interpretation report by a doctor of a medical department that is a request source.

As shown in FIG. 1, the information processing system 1 includes an imaging apparatus 2, an interpretation work station (WS) 3 that is an interpretation terminal, a medical care WS 4, an image server 5, an image database (DB) 6, a report server 7, and a report DB 8. The imaging apparatus 2, the interpretation WS 3, the medical care WS 4, the image server 5, the image DB 6, the report server 7, and the report DB 8 are connected to each other via a wired or wireless network 9 in a communicable state.

Each apparatus is a computer on which an application program for causing each apparatus to function as a component of the information processing system 1 is installed. The application program may be recorded on, for example, a recording medium, such as a digital versatile disc (DVD) or a compact disc read-only memory (CD-ROM), and distributed, and be installed on the computer from the recording medium. In addition, the application program may be stored in, for example, a storage device of a server computer connected to the network 9 or in a network storage in a state in which it can be accessed from the outside, and be downloaded and installed on the computer in response to a request.

The imaging apparatus 2 is an apparatus (modality) that generates a medical image T showing a diagnosis target part of the subject by imaging the diagnosis target part. Specifically, it is a simple X-ray imaging apparatus, a computed tomography (CT) apparatus, a magnetic resonance imaging (MRI) apparatus, a positron emission tomography (PET) apparatus, and the like. The medical image generated by the imaging apparatus 2 is transmitted to the image server 5 and is stored in the image DB 6.

The interpretation WS 3 is a computer used by, for example, a healthcare professional such as a radiologist of a radiology department to interpret a medical image and to create an interpretation report, and encompasses an information processing apparatus 10 according to the present embodiment. In the interpretation WS 3, a viewing request for a medical image to the image server 5, various types of image processing for the medical image received from the image server 5, display of the medical image, and input reception of a sentence regarding the medical image are performed. In the interpretation WS 3, analysis processing for medical images, support for creating an interpretation report based on the analysis result, a registration request and a viewing request for the interpretation report to the report server 7, and display of the interpretation report received from the report server 7 are performed. The above processes are performed by the interpretation WS 3 executing software programs for respective processes.

The medical care WS 4 is a computer used by, for example, a healthcare professional such as a doctor in a medical department to observe a medical image in detail, view an interpretation report, create an electronic medical record, and the like, and is configured to include a processing device, a display device such as a display, and an input device such as a keyboard and a mouse. In the medical care WS 4, a viewing request for the medical image to the image server 5, display of the medical image received from the image server 5, a viewing request for the interpretation report to the report server 7, and display of the interpretation report received from the report server 7 are performed. The above processes are performed by the medical care WS 4 executing software programs for respective processes.

The image server 5 is a general-purpose computer on which a software program that provides a function of a database management system (DBMS) is installed. The image server 5 is connected to the image DB 6. The connection form between the image server 5 and the image DB 6 is not particularly limited, and may be a form connected by a data bus, or a form connected to each other via a network such as a network attached storage (NAS) and a storage area network (SAN).

The image DB 6 is realized by, for example, a storage medium such as a hard disk drive (HDD), a solid-state drive (SSD), and a flash memory. In the image DB 6, the medical image acquired by the imaging apparatus 2 and accessory information attached to the medical image are registered in association with each other.

The accessory information may include, for example, identification information such as an image identification (ID) for identifying a medical image, a tomographic ID assigned to each tomographic image included in the medical image, a subject ID for identifying a subject, and an examination ID for identifying an examination. In addition, the accessory information may include, for example, information related to imaging such as an imaging method, an imaging condition, and an imaging date and time related to imaging of a medical image. The "imaging method" and "imaging condition" are, for example, a type of the imaging apparatus 2, an imaging part, an imaging protocol, an imaging sequence, an imaging method, the presence or absence of use of a contrast medium, a slice thickness in tomographic imaging, and the like. In addition, the accessory information may include information related to the subject such as the name, age, and gender of the subject.

In a case in which the image server 5 receives a request to register a medical image from the imaging apparatus 2, the image server 5 prepares the medical image in a format for a database and registers the medical image in the image DB 6. In addition, in a case in which the viewing request from the interpretation WS 3 and the medical care WS 4 is received, the image server 5 searches for a medical image registered in the image DB 6 and transmits the found medical image to the interpretation WS 3 and to the medical care WS 4 that are viewing request sources.

The report server 7 is a general-purpose computer on which a software program that provides a function of a database management system is installed. The report server 7 is connected to the report DB 8. The connection form between the report server 7 and the report DB 8 is not particularly limited, and may be a form connected by a data bus or a form connected via a network such as a NAS and a SAN.

The report DB 8 is realized by, for example, a storage medium such as an HDD, an SSD, and a flash memory. In the report DB 8, an interpretation report created in the interpretation WS 3 is registered.

Further, in a case in which the report server 7 receives a request to register the interpretation report from the interpretation WS 3, the report server 7 prepares the interpretation report in a format for a database and registers the interpretation report in the report DB 8. Further, in a case in which the report server 7 receives the viewing request for the interpretation report from the interpretation WS 3 and the medical care WS 4, the report server 7 searches for the interpretation report registered in the report DB 8, and transmits the found interpretation report to the interpretation WS 3 and to the medical care WS 4 that are viewing request sources. The network 9 is, for example, a network such as a local area network (LAN) and a wide area network (WAN). The imaging apparatus 2, the interpretation WS 3, the medical care WS 4, the image server 5, the image DB 6, the report server 7, and the report DB 8 included in the information processing system 1 may be disposed in the same medical institution, or may be disposed in different medical institutions or the like. Further, the number of each apparatus of the imaging apparatus 2, the interpretation WS 3, the medical care WS 4, the image server 5, the image DB 6, the report server 7, and the report DB 8 is not limited to the number shown in FIG. 1, and each apparatus may be composed of a plurality of apparatuses having the same functions.

Figure 2:
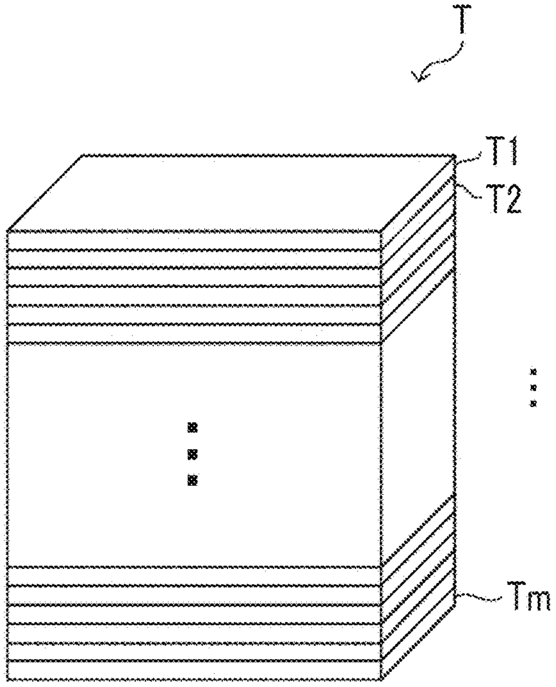
FIG. 2 is a diagram showing an example of a medical image.

FIG. 2 is a diagram schematically showing an example of a medical image acquired by the imaging apparatus 2. A medical image T shown in FIG. 2 is, for example, a CT image consisting of a plurality of tomographic images T1 to Tm (m is 2 or more) representing tomographic planes from the head to the waist of one subject (human body).

Figure 3:
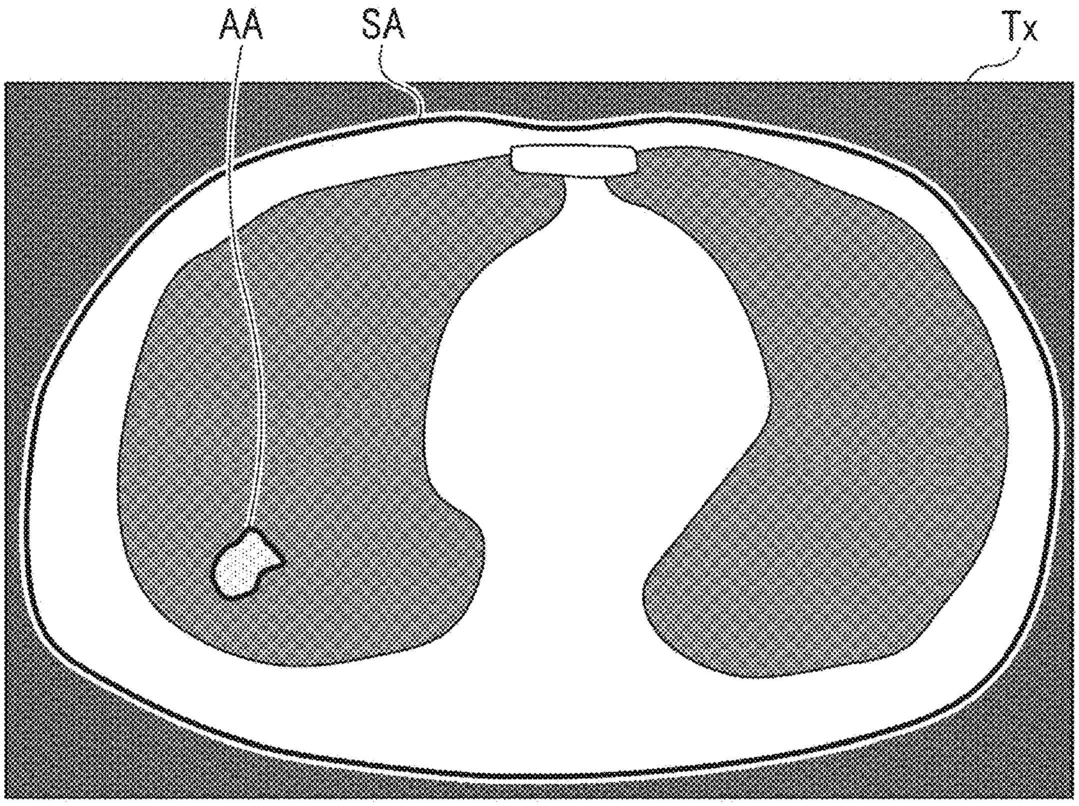
FIG. 3 is a diagram showing an example of a medical image.

FIG. 3 is a diagram schematically showing an example of one tomographic image Tx out of the plurality of tomographic images T1 to Tm. The tomographic image Tx shown in FIG. 3 represents a tomographic plane including lungs. Each of the tomographic images T1 to Tm may include a region SA of a structure showing various organs and viscera of the human body (for example, lungs, livers, and the like), various tissues constituting various organs and viscera (for example, blood vessels, nerves, muscles, and the like), and the like. In addition, each tomographic image may include a region AA of an abnormal shadow showing lesions such as, for example, nodules, tumors, injuries, defects, and inflammation. In the tomographic image Tx shown in FIG. 3, the lung region is the region SA of the structure, and the nodule region is the region AA of the abnormal shadow. Hereinafter, at least one of the region SA of the structure or the region AA of the abnormal shadow is referred to as a "region of interest". Note that one tomographic image may include a plurality of regions of interest.

Incidentally, an interpretation report may include a plurality of comments on findings that differ in content, such as a structure to be described, a lesion, and an imaging date and time of a medical image. For case of reading, it is desirable to consider the description order of a plurality of comments on findings included in an interpretation report, and to describe comments on findings with similar contents together. Therefore, the information processing apparatus 10 according to the present embodiment has a function of supporting creation of an interpretation report in consideration of the description order of the comments on findings. The information processing apparatus 10 will be described below. As described above, the information processing apparatus 10 is encompassed in the interpretation WS 3.

Figure 4:
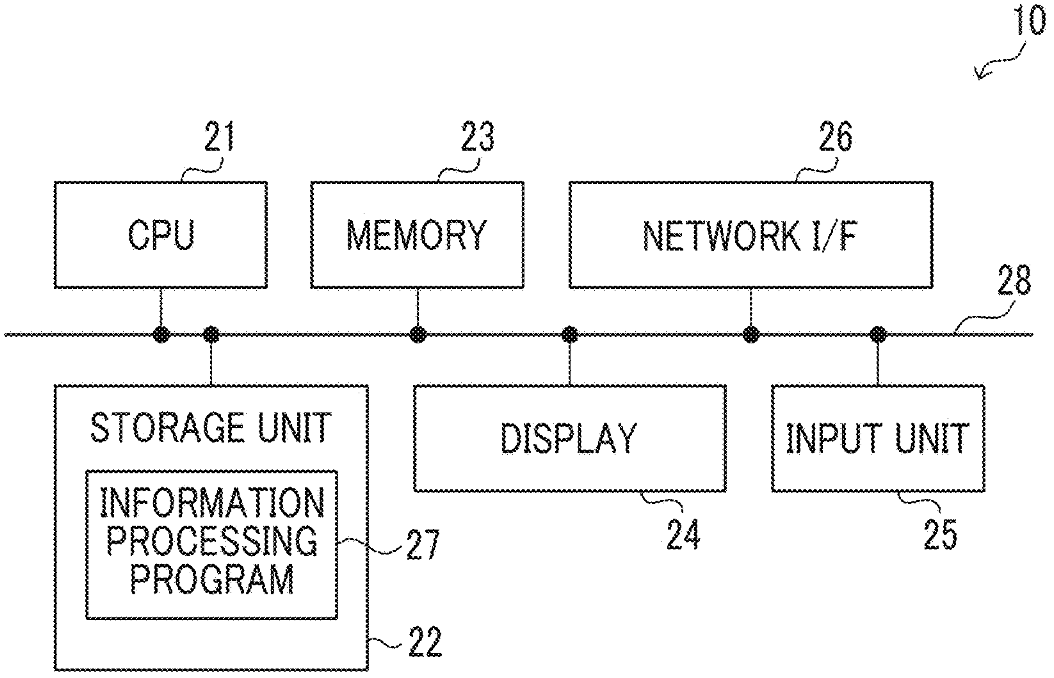
FIG. 4 is a block diagram showing an example of a hardware configuration of an information processing apparatus.

First, with reference to FIG. 4, an example of a hardware configuration of the information processing apparatus 10 according to the present embodiment will be described. As shown in FIG. 4, the information processing apparatus 10 includes a central processing unit (CPU) 21, a non-volatile storage unit 22, and a memory 23 as a temporary storage area. Further, the information processing apparatus 10 includes a display 24 such as a liquid crystal display, an input unit 25 such as a keyboard and a mouse, and a network interface (I/F) 26. The network I/F 26 is connected to the network 9 and performs wired or wireless communication. The CPU 21, the storage unit 22, the memory 23, the display 24, the input unit 25, and the network I/F 26 are connected to each other via a bus 28 such as a system bus and a control bus so that various types of information can be exchanged.

The storage unit 22 is realized by, for example, a storage medium such as an HDD, an SSD, and a flash memory. An information processing program 27 in the information processing apparatus 10 is stored in the storage unit 22. The CPU 21 reads out the information processing program 27 from the storage unit 22, loads the read-out program into the memory 23, and executes the loaded information processing program 27. The CPU 21 is an example of a processor of the present disclosure. As the information processing apparatus 10, for example, a personal computer, a server computer, a smartphone, a tablet terminal, a wearable terminal, or the like can be applied as appropriate.

Figure 5:
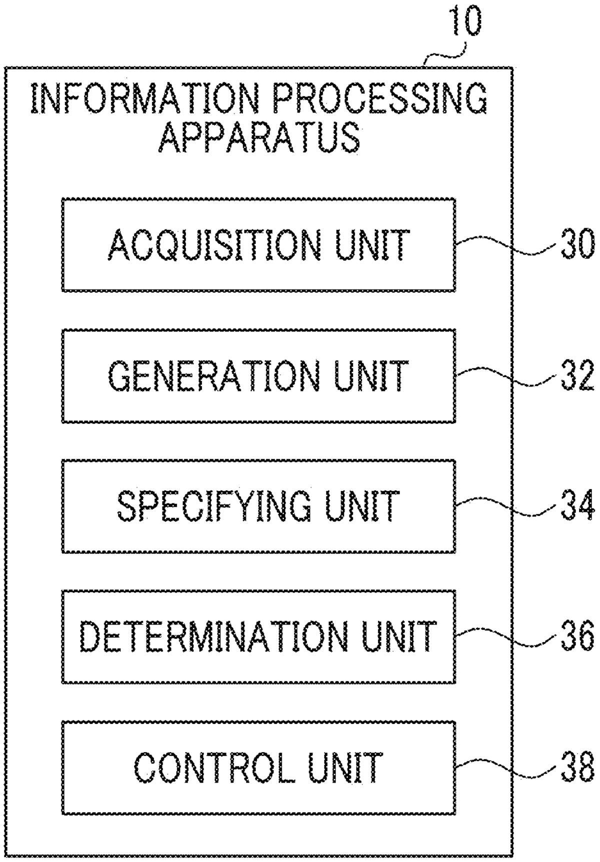
FIG. 5 is a block diagram showing an example of a functional configuration of the information processing apparatus.

Next, with reference to FIG. 5, an example of a functional configuration of the information processing apparatus 10 according to the present embodiment will be described. As shown in FIG. 5, the information processing apparatus 10 includes an acquisition unit 30, a generation unit 32, a specifying unit 34, a determination unit 36, and a control unit 38. In a case in which the CPU 21 executes the information processing program 27, the CPU 21 functions as the acquisition unit 30, the generation unit 32, the specifying unit 34, the determination unit 36, and the control unit 38.

(Acquisition of Existing Sentences and Generation of New Sentences)

Figure 6:
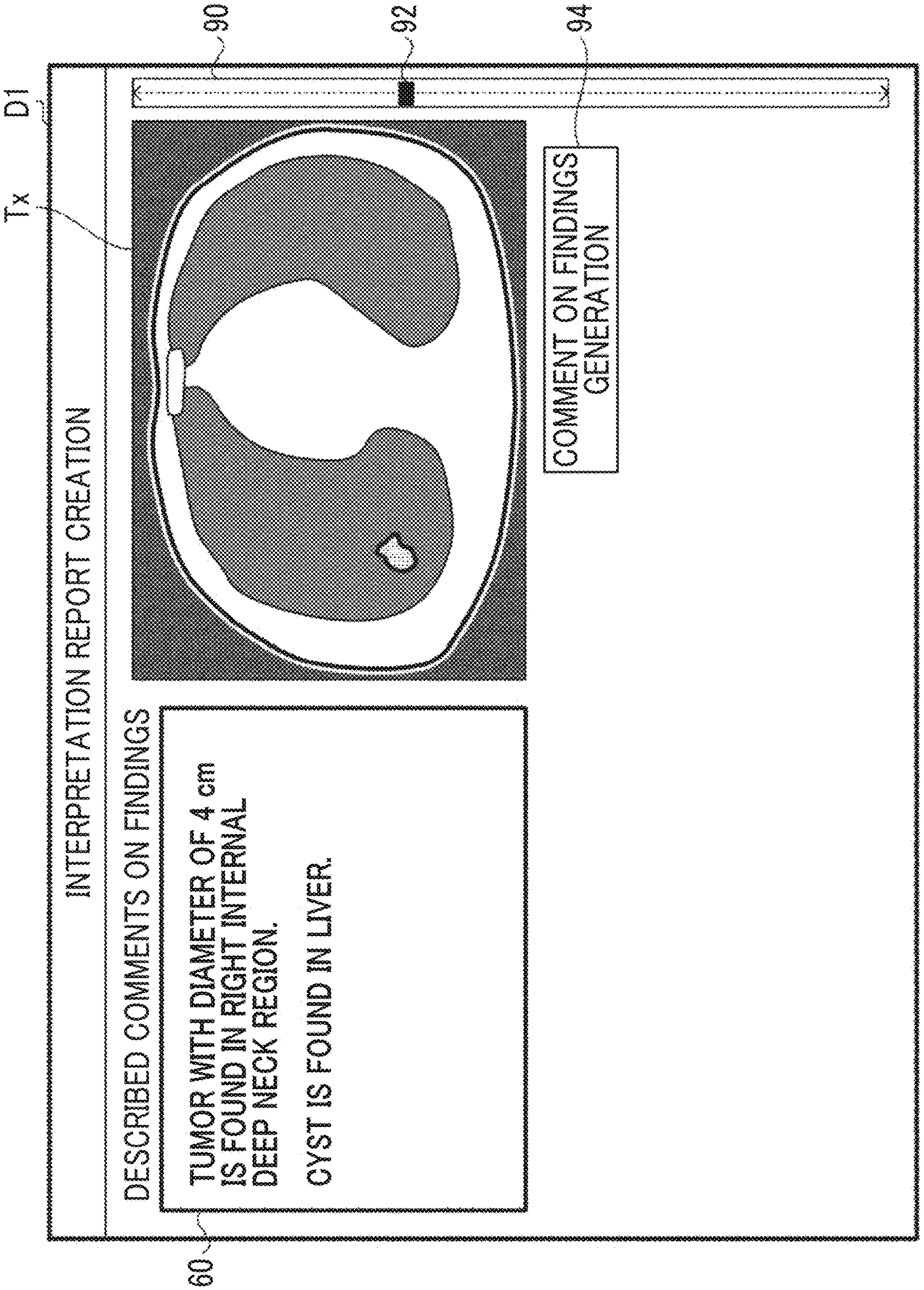
FIG. 6 is a diagram showing an example of a screen displayed on a display.

First, the functions of each processing unit related to acquisition and generation of a plurality of comments on findings included in the interpretation report will be described with reference to FIGS. 6 and 7.

The acquisition unit 30 acquires, from the image server 5, at least one medical image for which an interpretation report is to be created. For example, the acquisition unit 30 may acquire a CT image consisting of a plurality of tomographic images T1 to Tm. Further, for example, the acquisition unit 30 may acquire a plurality of medical images related to the same subject, such as a plurality of medical images (for example, a combination of a simple CT image, a contrast CT image, and an MRI image) having different types of imaging apparatuses 2, imaging conditions, and imaging methods.

In addition, the acquisition unit 30 acquires an interpretation report that is described for a subject that is the same as the subject of the acquired medical image and already includes at least one comment on findings from the report server 7, the storage unit 22, and the like. This interpretation report may be, for example, temporarily stored during creation, created by another radiologist in a case in which the radiologist is different for each medical image (for example, each organ), or created in the past. Hereinafter, the comments on findings that have already been described in the interpretation report will be referred to as existing sentences 60.

The control unit 38 performs control to display the medical image and the existing sentences 60 acquired by the acquisition unit 30 on the display 24. FIG. 6 shows an example of a screen D1 displayed on the display 24 by the control unit 38. The screen D1 includes the medical image Tx acquired by the acquisition unit 30 and the existing sentences 60.

Further, the screen D1 includes a slider bar 90 for receiving an operation of selecting an image to be displayed on the display 24 from a plurality of tomographic images T1 to Tm. The slider bar 90 is a graphical user interface (GUI) part that is also called a slide bar or a scroll bar. An example of the screen D1 corresponds to a plurality of tomographic images T1 to Tm arranged in order from the head side to the waist side from the upper end to the lower end.

The control unit 38 receives an operation of the position of a slider 92 on the slider bar 90 by the user via the input unit 25, and displays, on the screen D1, one image (the tomographic image Tx in the example of FIG. 6) corresponding to the position of the slider 92 among the plurality of tomographic images T1 to Tm. The dotted arrow added to the slider 92 in FIG. 6 means the movable range of the slider 92 in the slider bar 90.

Further, the screen D1 includes a comment-on-findings generation button 94. In a case in which the comment-on-findings generation button 94 is selected by the user, the generation unit 32 generates at least one comment on findings based on the medical image (in particular, the tomographic image Tx displayed on the screen D1 by the operation of the slider 92) acquired by the acquisition unit 30. Hereinafter, the comment on findings newly generated by the generation unit 32 will be referred to as a new sentence 62.

Specifically, first, the generation unit 32 analyzes a medical image using CAD or the like and detects a region of interest included in the medical image. As a method for detecting a region of interest, for example, a trained model such as convolutional neural network (CNN), which has been trained in advance so that the input is a medical image and the output is the region of interest detected from the medical image, may be used. This trained model is, for example, a model trained by machine learning using a large number of medical images in which a region of interest, that is, a region having a predetermined physical feature, is known, as training data. The "region having a physical feature" includes, for example, a region in a range in which the pixel value is set in advance (for example, a region in which the pixel value is relatively white/black mass compared to the surroundings) and a region having a preset shape. For example, a region in the medical image designated by the user via the input unit 25 may be detected as the region of interest.

Next, the generation unit 32 generates medical information 70 indicating a name (type), a property, a measured value, a position, an estimated disease name (including a negative or positive evaluation result), etc. related to the detected region of interest. As a method of generating the medical information 70, for example, a trained model such as CNN, which has been trained in advance so that the input is the region of interest detected from the medical image and the output is the medical information 70 related to the region of interest, may be used.

Examples of names (types) include the names of structures such as "lung" and "liver", and the names of abnormal shadows such as "lung nodule" and "liver cyst". The property mainly means the features of abnormal shadows. For example, in the case of a lung nodule, findings indicating opacity such as "solid" and "ground-glass", margin shapes such as "well-defined/ill-defined", "smooth/irregular", "spicula", "lobulated", and "lagged", and an overall shape such as "round" and "irregular form" can be mentioned. Also, for example, the relationship with the peripheral tissue, such as "pleural contact" and "pleural invagination", and findings regarding the presence or absence of contrast, washout, and the like can be mentioned.

The measured value is a value that can be quantitatively measured from a medical image, and examples thereof include a size (a major axis, a minor axis, a volume, and the like), a CT value whose unit is HU, the number of regions of interest in a case in which there are a plurality of regions of interest, and a distance between regions of interest. Further, the measured value may be replaced with a qualitative expression such as "large/small" or "more/less". The position means an anatomical position, a position in a medical image, and a relative positional relationship with other regions of interest such as "inside", "margin", and "periphery". The anatomical position may be indicated by an organ name such as "lung" and "liver", and may be expressed in terms of subdivided lungs such as "right lung", "upper lobe", and apical segment ("S1"). The estimated disease name is an evaluation result estimated by the generation unit 32 based on the abnormal shadow, and, for example, the disease name such as "cancer" and "inflammation" and the evaluation result such as "negative/positive", "benign/malignant", and "mild/severe" regarding disease names and properties can be mentioned.

Note that the medical information 70 is not limited to that generated based on medical images. For example, the generation unit 32 may generate the medical information 70 based on information input by the user via the input unit 25. In addition, as described above, each medical image is attached by accessory information including information related to imaging at the point in time of being registered in the image DB 6. Therefore, for example, the generation unit 32 may generate, as the medical information 70, information indicating at least one of an imaging method, an imaging condition, or an imaging date and time related to the imaging of the medical image based on the accessory information attached to the medical image acquired from the image server 5.

Further, for example, the generation unit 32 may acquire medical information 70 generated in advance by an external device having a function of generating the medical information 70 based on a medical image as described above from the external device. Further, for example, the generation unit 32 may acquire various types of information included in an examination order and an electronic medical record, information indicating various test results such as a blood test and an infectious disease test, information indicating the result of a health diagnosis, and the like from the external device such as the medical care WS 4, and generate the acquired information as the medical information 70 as appropriate.

That is, the generation unit 32 may acquire medical information 70 related to a medical image by generating the medical information 70 based on at least one of the medical image, information input via the input unit 25, or accessory information, acquiring the medical information 70 from an external device, or the like. In addition, in a case in which a plurality of regions of interest are included in one medical image, the generation unit 32 may generate and/or acquire medical information 70 related to each of the plurality of regions of interest included in the medical image. In addition, in a case in which there are a plurality of medical images for which an interpretation report is to be created, the generation unit 32 may generate and/or acquire medical information 70 related to each of the plurality of medical images.

Thereafter, the generation unit 32 generates a new sentence 62 including the description based on the generated and/or acquired medical information 70. In this case, it is preferable that the generation unit 32 generates a plurality of candidates of the new sentences 62 by changing the combination of medical information 70 included in the comment on findings. This is because there are users who prefer a concise comment on findings that only describes important findings, while users who prefer a rich comment on findings that describes findings including negative findings, and it is preferable to present a plurality of options. As a method of generating the new sentence 62, for example, a learning model in which machine learning is performed, such as the recurrent neural network described in JP2019-153250A can be applied.

The control unit 38 controls the display 24 to display the new sentence 62 generated by the generation unit 32. FIG. 7 shows an example of a screen D2 displayed on the display 24 by the control unit 38. The screen D2 includes a plurality of candidates of new sentences 62-1 to 62-3 generated by the generation unit 32. The control unit 38 receives selection of any one of the plurality of candidates of the new sentences 62-1 to 62-3. In the example in FIG. 7, the new sentence 62-2 is selected.

Figure 7:
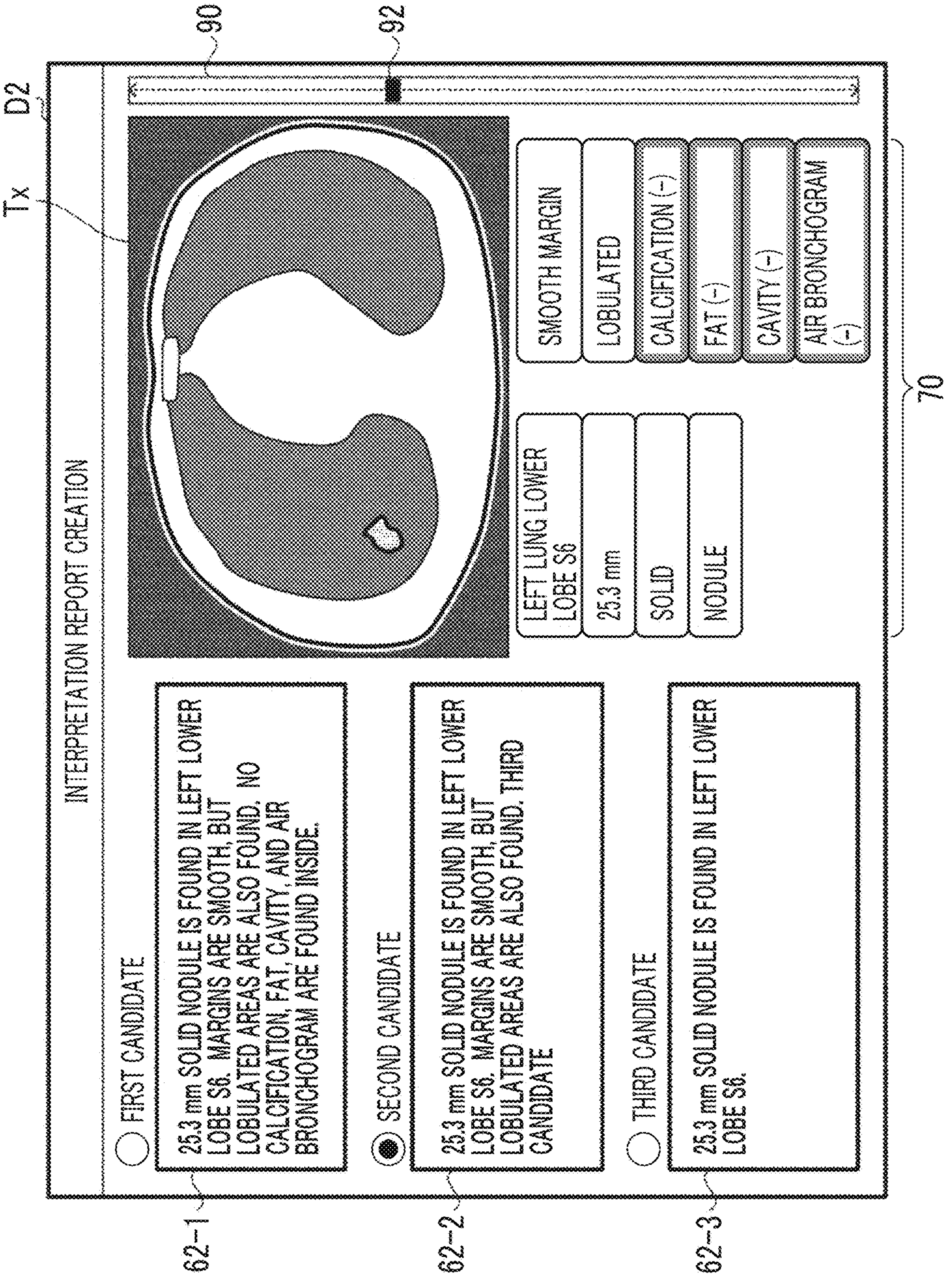
FIG. 7 is a diagram showing an example of a screen displayed on a display.

In addition, as shown in FIG. 7, the screen D2 may include a label showing the medical information 70 generated based on the tomographic image Tx. In FIG. 7, labels indicating negative medical information 70 are marked with "(−)", and the labels are color-coded for positive and negative. By displaying the labels indicating the medical information 70 on the display 24, the user can easily ascertain the content of the medical image (tomographic image Tx) and the new sentence 62.

As described above, the existing sentence 60 and the new sentence 62 are sentences in which mutually different medical information of the same subject is described. Further, at least one of the existing sentence 60 or the new sentence 62 may include a sentence generated based on a medical image.

(Rearrangement of Comments on Findings)

Next, the functions of each processing unit related to the rearrangement of the existing sentence and the new sentence will be described with reference to FIGS. 8 and 9. In the following description, the description will be made using the existing sentence 60 shown in FIG. 6 as the existing sentence and using a second candidate of a new sentence 62-2 shown in FIG. 7 as the new sentence.

As described above, the acquisition unit 30 acquires at least one existing sentence 60 from the report server 7, the storage unit 22, and the like. Further, the acquisition unit 30 acquires a new sentence 62 described after the existing sentence 60, which is generated by the generation unit 32.

The specifying unit 34 specifies medical information 72 from each of the existing sentence 60 and the new sentence 62. Specifically, the specifying unit 34 specifies at least one word representing the medical information 72 included in the existing sentence 60 and the new sentence 62 acquired by the acquisition unit 30. As a method for specifying words included in a comment on findings, a known named entity extraction method using a natural language processing model such as, for example, bidirectional encoder representations from transformers (BERT) can be applied as appropriate.

Alternatively, for example, a word included in the comments on findings may be specified by storing a word representing the medical information 72 in the storage unit 22 as a dictionary in advance and referring to the dictionary.

The medical information 72 specified from the existing sentence 60 and the new sentence 62 by the specifying unit 34 is the same information as the medical information 70 generated from a medical image or the like by the generation unit 32 described above. Specifically, the medical information 72 may be information indicating at least one of a type of an organ, a type of a lesion, or a type of an examination. FIG. 8 shows an example of medical information 72 specified from each of existing sentences 60A and 60B obtained by dividing the existing sentence 60 and the new sentence 62. FIG. 8 shows types of organs ("neck", "liver", and "lung") described in each comment on findings as an example of the medical information 72. As shown in FIG. 8, in a case in which a plurality of sentences are included in the existing sentence 60 and the new sentence 62, the specifying unit 34 may specify the medical information 72 in units of sentences.

Figure 8:
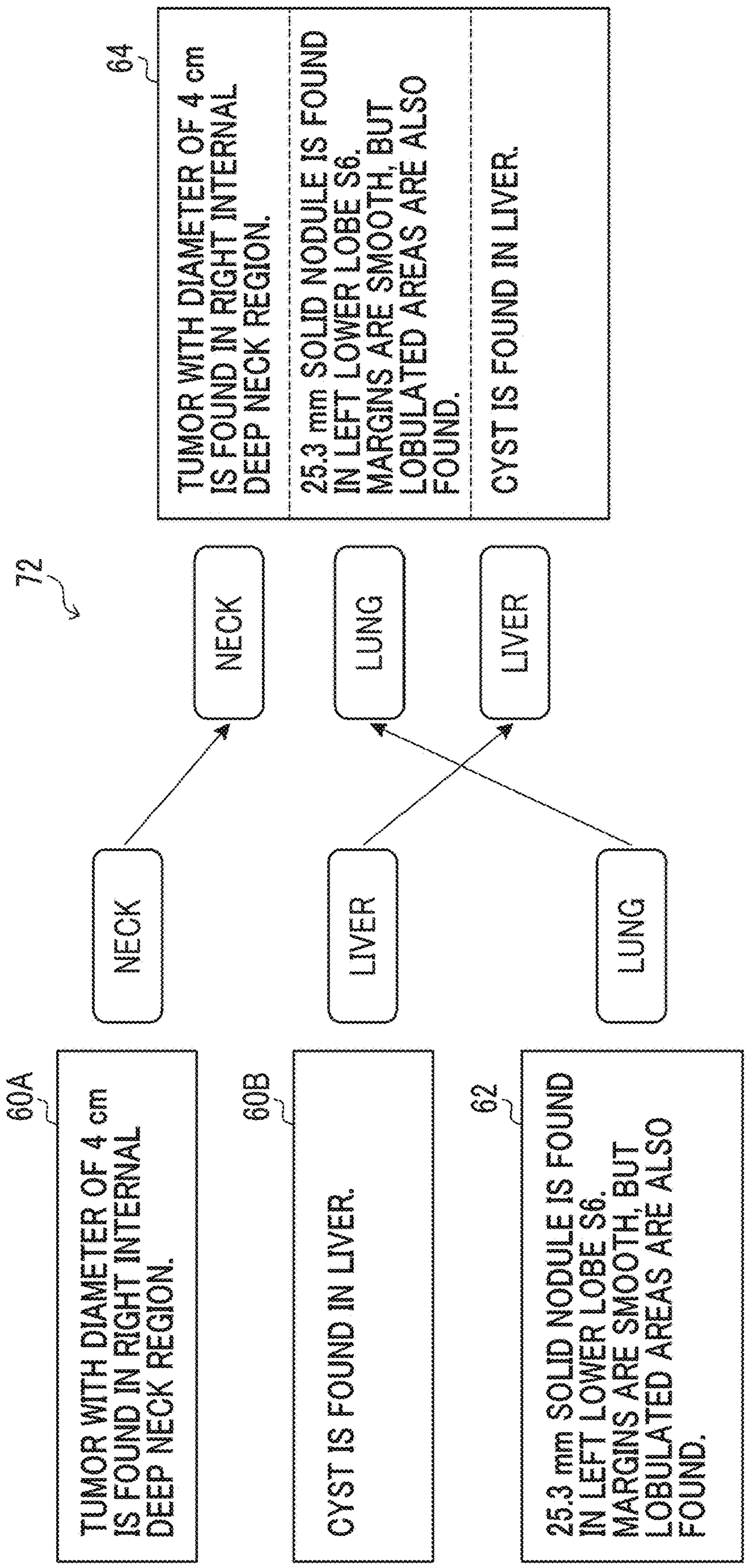
FIG. 8 is a diagram for describing rearrangement of comments on findings.

Further, the new sentence 62 shown in FIG. 8 does not include the word "lungs", but includes a word "left lower lobe S6" representing the lung region. In this way, the specifying unit 34 may specify, as the medical information 72 included in the comments on findings, not only the medical information 72 indicating the words itself included in the comments on findings ("left lower lobe S6") but also other related medical information 72 ("lungs").

Further, in a case of the new sentence 62, the generation unit 32 generates the medical information 70 in a process of generating the new sentence 62 as described above. The specifying unit 34 may use the medical information 70 generated by the generation unit 32 based on a medical image or the like to specify the medical information 72 included in the new sentence 62.

The determination unit 36 determines an arrangement order of the existing sentences 60 (60A and 60B) and the new sentence 62 in accordance with a predetermined rule based on the medical information 72 described in each of the existing sentences 60 (60A and 60B) and the new sentence 62 specified by the specifying unit 34. The predetermined rules may be stored in the storage unit 22, for example.

Specifically, the determination unit 36 may determine the arrangement order such that the existing sentence 60 and the new sentence 62 are arranged for each type of the medical information 72 (that is, a type of an organ, a type of a lesion, a type of an examination, and the like). In the example in FIG. 8, the medical information 72 (the "neck", the "liver", and the "lung") indicating the type of the organ included in each of the existing sentences 60 (60A and 60B) and the new sentence 62 is rearranged in the order of the "neck", the "lung", and the "liver" to be arranged in order from the head side to the waist side of the human body.

The control unit 38 rearranges the existing sentences 60 (60A and 60B) and the new sentence 62 based on the arrangement order determined by the determination unit 36, and generates one comment on findings (hereinafter referred to as a "combined sentence 64") by summarizing the rearranged sentences. The combined sentence 64 generated in this way is an easy-to-read sentence in which the existing sentences 60 (60A and 60B) and the new sentence 62 are arranged in accordance with a predetermined rule.

Further, the control unit 38 controls the display 24 to display the generated combined sentence 64. FIG. 9 shows an example of a screen D3 displayed on the display 24 by the control unit 38. The screen D3 includes the combined sentence 64. As shown in FIG. 9, the control unit 38 may perform control to display the combined sentence 64 (the existing sentence 60 and the new sentence 62 after rearrangement) on the display 24 by highlighting a portion corresponding to the new sentence 62 in the combined sentence 64. As means for highlighting, for example, in addition to an underline 98 as shown in FIG. 9, a color, a size, a thickness, an italic, a type, and the like of a font may be changed, a background color of a font may be changed, or the font may be surrounded by a bounding box.

Figure 9:
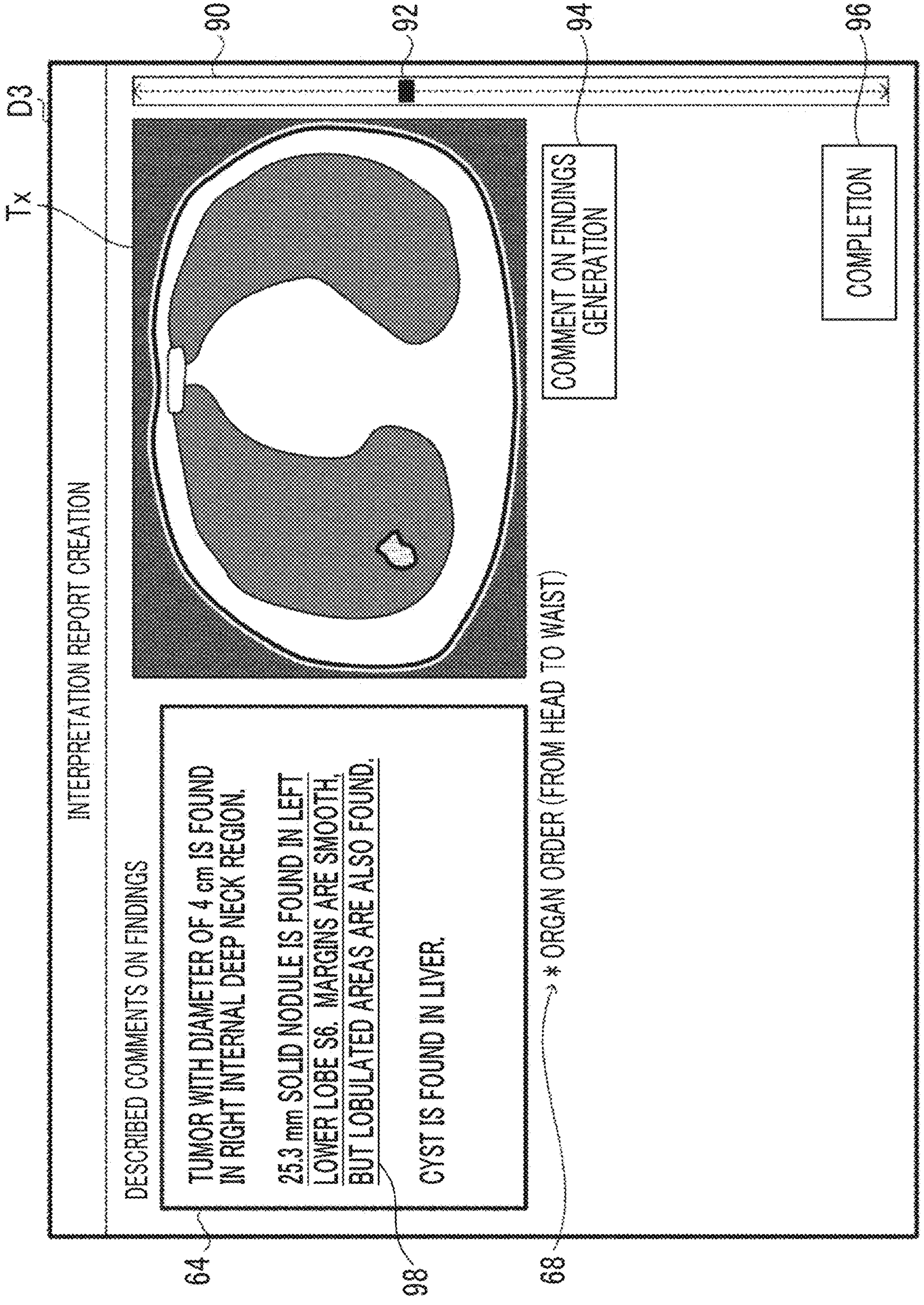
FIG. 9 is a diagram showing an example of a screen displayed on a display.

Further, as shown in FIG. 9, it is preferable that the control unit 38 displays information 68 indicating the rule for the arrangement order in the combined sentence 64 on the display 24. The screen D3 includes wording "organ order (from the head to the waist)" as information 68 indicating the rule for the arrangement order.

In a case in which a comment on findings regarding another tomographic image to the combined sentence 64 is further added, the user operates the slider 92 on the slider bar 90 on the screen D3 to display the tomographic image for which a comment on findings is to be generated on the screen D3, and then selects the comment-on-findings generation button 94. In a case in which the comment-on-findings generation button 94 is selected by the user, each processing unit repeatedly performs the above-described generation process and rearrangement process of the new sentence 62, using the combined sentence 64 as the existing sentence 60 and the newly added comment on findings as the new sentence 62.

On the other hand, in a case in which the creation of the interpretation report is completed, the user selects a completion button 96 included in the screen D3. In a case in which the user selects the completion button 96, the control unit 38 requests the report server 7 to register the interpretation report including the combined sentence 64.

(Rules for Arrangement Order)

In the above description, an example in which the existing sentence 60 and the new sentence 62 are rearranged for each type of the medical information 72 has been described, but the rule for the arrangement order of the existing sentence 60 and the new sentence 62 is not limited thereto. Other examples of rules for an arrangement order will be described below.

For example, the determination unit 36 may determine the arrangement order such that the existing sentence 60 and the new sentence 62 are arranged for each property of the medical information 72 indicating the properties of the lesion. For example, in a case in which both the existing sentence 60 and the new sentence 62 describe the lung nodule, the determination unit 36 may rearrange the existing sentence 60 and the new sentence 62 to be arranged in the order of the overall shape, the shape of the margin, and the relationship with the peripheral tissue. Further, for example, the determination unit 36 may rearrange the existing sentence 60 and the new sentence 62 such that the positive finding is positioned at the beginning of the sentence and the negative finding is positioned at the end of the sentence.

In addition, for example, the specifying unit 34 may specify a factuality regarding the medical information 72 from each of the existing sentence 60 and the new sentence 62, and the determination unit 36 may determine the arrangement order such that the existing sentences 60 and the new sentences 62 are arranged for each factuality regarding the medical information 72 specified by the specifying unit 34. The factuality means the presence or absence and the accuracy of a lesion, a property, a disease name, and the like. This is because, for example, the interpretation report includes a comment on findings regarding a lesion, a property, and a disease name that are not certain, such as "lung adenocarcinoma is suspected", and intentional descriptions of a lesion, a property, and a disease name that do not exist, such as "no spicula is found". For example, the determination unit 36 may rearrange the existing sentence 60 and the new sentence 62 such that the comments on findings regarding the lesion, the property, and the disease name having a high probability are positioned at the beginning of the sentence, and the comments on findings regarding the lesion, the property, and the disease name having a low probability or not having a probability are positioned at the end of the sentence.

Further, for example, the determination unit 36 may determine an arrangement order such that the existing sentence 60 and the new sentence 62 are arranged in the order of importance of the medical information 72 whose importance is predetermined. For example, the determination unit 36 may determine the arrangement order such that the existing sentence 60 and the new sentence 62 with a higher importance of the medical information 72 are positioned closer to the beginning of the sentence. The importance of the medical information 72 may be set in advance, for example, or may be optionally settable by the user.

For example, the importance may be set high for properties that have a high risk of becoming more serious. Furthermore, for example, the importance of the organ and the lesion reported as the medical history of the subject may be set to be high. Further, for example, an organ that is examined many times, a lesion, and the importance of the examination may be set to be high.

In addition, for example, the determination unit 36 may determine the arrangement order such that the existing sentence 60 and the new sentence 62 are arranged in chronological order of the medical information 72 indicating a point in time at which an examination is performed. The medical information 72 indicating a point in time at which an examination is performed is, for example, the imaging date and time of the medical image, and the examination date and time of various tests (for example, blood test, infectious disease test, and the like). For example, in a case in which the medical image is captured a plurality of times, the determination unit 36 may rearrange the existing sentence 60 and the new sentence 62 such that the comment on findings regarding the medical image with a new imaging date and time is positioned at the beginning of the sentence.

Further, for example, the determination unit 36 may determine the arrangement order based on whether or not the medical information 72 corresponding to the existing sentence 60 and the new sentence 62 is included in the past document. Specifically, the acquisition unit 30 acquires, from the report server 7, a past document including a sentence describing medical information 72 of the subject for whom an interpretation report is currently being created. In other words, the past document is, for example, an interpretation report created at a past point in time. In a case in which the past document acquired by the acquisition unit 30 includes the same medical information 72 as the existing sentence 60 and the new sentence 62, the determination unit 36 may rearrange the existing sentence 60 and the new sentence 62 such that the comment on findings regarding the medical information 72 is positioned at the beginning of the sentence.

Further, the rules regarding the arrangement order may be applied in combination as appropriate. For example, after rearranging a plurality of comments on findings in the order of the organs of the neck, the lung, and the liver, only a plurality of comments on findings regarding the lung may be rearranged in the order of importance such that the order of the organs is not broken.

Note that in a case in which there are a plurality of existing sentences 60 (60A and 60B), the determination unit 36 may determine the arrangement order for determining the insertion position of the new sentence 62 while an arrangement order of the plurality of existing sentences 60 (60A and 60B) is fixed. That is, the determination unit 36 may determine the arrangement order that only determines in which position in the existing sentence 60 the new sentence 62 is to be inserted. On the other hand, in a case in which there are a plurality of existing sentences 60 (60A and 60B), the determination unit 36 may determine the arrangement order including the rearrangement of the existing sentences 60 (60A and 60B).

In addition, for example, in a case in which the new sentence 62 is further added to the combined sentence 64, that is, in a case in which the existing sentence 60 and the new sentence 62 are repeatedly rearranged, the rearrangement including the existing sentence 60 may be performed only for the first time, and the arrangement order of the existing sentence 60 may be fixed for the second and subsequent times. In addition, in a case in which the rearrangement of the existing sentences 60 is also performed, the control unit 38 may perform control to highlight the rearranged existing sentences 60 and to display the combined sentence 64 (the existing sentence 60 and the new sentence 62 after the rearrangement) on the display 24.

For example, the rule for the arrangement order and whether to fix the arrangement order of the existing sentences 60 or to rearrange sentences including the existing sentences 60 may be set in advance or may be optionally selected by the user. Also, for example, it may be set in advance for each user and/or each subject.

Figure 10:
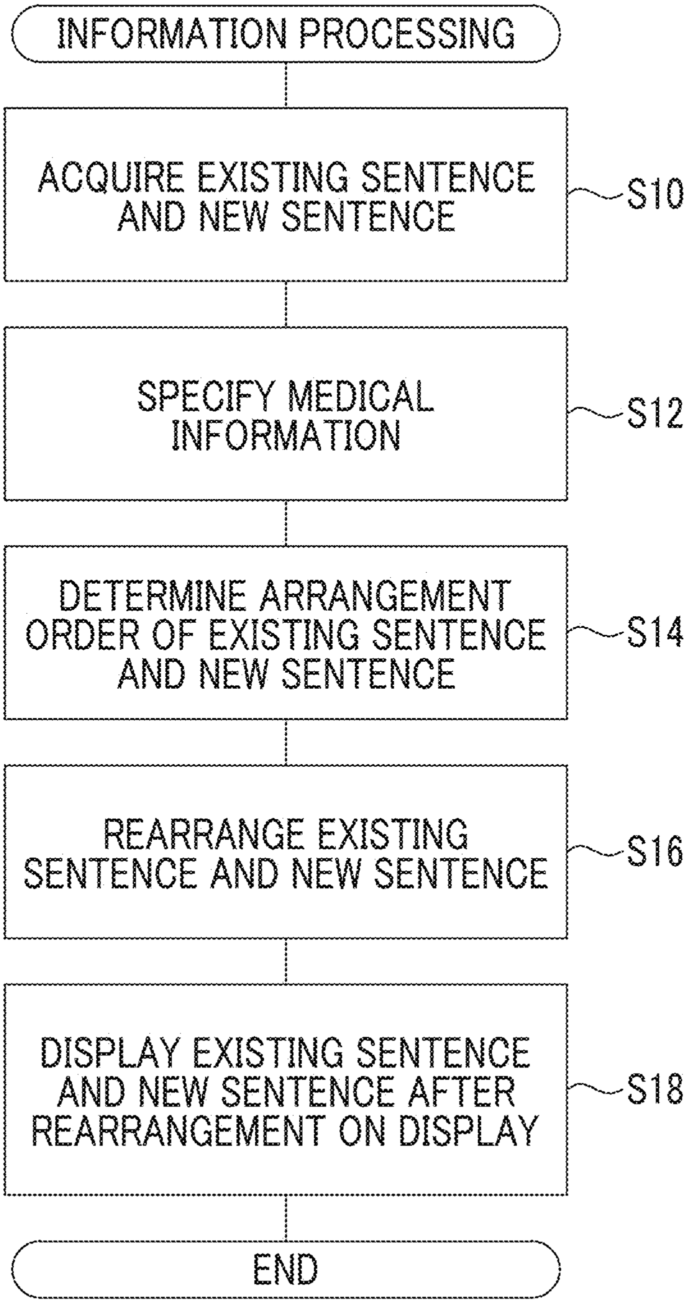
FIG. 10 is a flowchart showing an example of information processing.

Next, with reference to FIG. 10, operations of the information processing apparatus 10 according to the present embodiment will be described. In the information processing apparatus 10, the CPU 21 executes the information processing program 27, and thus first information processing shown in FIG. 10 is executed. The first information processing is executed, for example, in a case in which the user gives an instruction to start execution via the input unit 25.

In Step S10, the acquisition unit 30 acquires at least one existing sentence from the report server 7, the storage unit 22, and the like. Further, the acquisition unit 30 acquires the new sentence generated by the generation unit 32. In Step S12, the specifying unit 34 specifies medical information from each of the existing sentence and the new sentence acquired in Step S10.

In Step S14, the determination unit 36 determines the arrangement order of the existing sentence and the new sentence in accordance with a predetermined rule based on the medical information described in each of the existing sentence and the new sentence specified in Step S12. In Step S16, the control unit 38 rearranges the existing sentence and the new sentence based on the arrangement order determined in Step S14, and generates one combined sentence by summarizing the existing sentence and the new sentence. In Step S18, the control unit 38 performs control to display the combined sentence (the existing sentence and the new sentence after rearrangement) generated in Step S16 on the display 24, and ends the present information processing.

As described above, the information processing apparatus 10 according to one aspect of the present disclosure comprises at least one processor, in which the processor acquires at least one existing sentence and a new sentence described after the existing sentence, mutually different medical information of the same subject being described in the existing sentence and the new sentence; and determines an arrangement order of the existing sentence and the new sentence in accordance with a predetermined rule based on the medical information described in each of the existing sentence and the new sentence.

That is, with the information processing apparatus 10 according to the present embodiment, for an interpretation report that includes a plurality of comments on findings that differ in content, such as an organ to be described, a lesion, and an imaging date and time, it is possible to create an interpretation report that takes into account the description order of each comment on findings. Therefore, even in a case in which the user adds a new sentence without considering the description order, it is possible to create an easy-to-read interpretation report with a well-arranged description order, thereby supporting the creation of an interpretation report.

Note that in the above embodiment, the form in which the new sentence 62 is the comment on findings generated by the generation unit 32 based on the medical information has been described, but the present disclosure is not limited thereto. For example, at least one of the existing sentence 60 or the new sentence 62 may be a comment on findings input by a user.

In the above embodiment, for example, as hardware structures of processing units that execute various kinds of processing, such as the acquisition unit 30, the generation unit 32, the specifying unit 34, the determination unit 36, and the control unit 38, various processors shown below can be used. As described above, the various processors include a programmable logic device (PLD) as a processor of which the circuit configuration can be changed after manufacture, such as a field-programmable gate array (FPGA), a dedicated electrical circuit as a processor having a dedicated circuit configuration for executing specific processing such as an application-specific integrated circuit (ASIC), and the like, in addition to the CPU as a general-purpose processor that functions as various processing units by executing software (program).

One processing unit may be configured by one of the various processors, or may be configured by a combination of the same or different kinds of two or more processors (for example, a combination of a plurality of FPGAs or a combination of the CPU and the FPGA). In addition, a plurality of processing units may be configured by one processor.

As an example in which a plurality of processing units are configured by one processor, first, there is a form in which one processor is configured by a combination of one or more CPUs and software as typified by a computer, such as a client or a server, and this processor functions as a plurality of processing units. Second, as represented by a system-on-chip (SoC) or the like, there is a form of using a processor for realizing the function of the entire system including a plurality of processing units with one integrated circuit (IC) chip. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

In the above embodiment, the information processing program 27 is described as being stored (installed) in the storage unit 22 in advance; however, the present disclosure is not limited thereto. The information processing program 27 may be provided in a form recorded in a recording medium such as a compact disc read-only memory (CD-ROM), a digital versatile disc read-only memory (DVD-ROM), and a universal serial bus (USB) memory. In addition, the information processing program 27 may be configured to be downloaded from an external device via a network. Further, the technology of the present disclosure extends to a storage medium for storing the information processing program non-transitorily in addition to the information processing program.

The technology of the present disclosure can be combined as appropriate with the above embodiment. The described contents and illustrated contents shown above are detailed descriptions of the parts related to the technology of the present disclosure, and are merely an example of the technology of the present disclosure. For example, the above description of the configuration, function, operation, and effect is an example of the configuration, function, operation, and effect of the parts related to the technology of the present disclosure. Therefore, needless to say, unnecessary parts may be deleted, new elements may be added, or replacements may be made to the described contents and illustrated contents shown above within a range that does not deviate from the gist of the technology of the present disclosure.

The disclosure of JP2022-024251 filed on Feb. 18, 2022 is incorporated herein by reference in its entirety. All documents, patent applications, and technical standards described in the present specification are incorporated in the present specification by reference to the same extent as in a case in which each of the documents, patent applications, technical standards are specifically and individually indicated to be incorporated by reference.

What is claimed is:

1. An information processing apparatus comprising at least one processor, wherein the at least one processor is configured to:

input a region of interest included in a medical image to a trained model;

cause the trained model to output medical information indicating a name, a type, a property, a measured value, a position, and an estimated disease name including a negative or positive evaluation result, related to the region of interest;

generate a new sentence including a description based on the medical information;

acquire at least one existing sentence and the new sentence described after the existing sentence, mutually different medical information of the same subject being described in the existing sentence and the new sentence;

specify a word included in each of the existing sentence and the new sentence;

generate medical information data corresponding to the specified word, the medical information data representing medical information that is represented by or related to the specified word, and associate the generated medical information data with each of the existing sentence and the new sentence; and determine an arrangement order of the existing sentence and the new sentence in accordance with a predetermined rule based on the associated medical information data.

2. The information processing apparatus according to claim 1, wherein the at least one processor is configured to specify the medical information from each of the existing sentence and the new sentence.

3. The information processing apparatus according to claim 1, wherein the at least one processor is configured to determine, in a case in which there are a plurality of the existing sentences, the arrangement order including rearrangement of the existing sentences.

4. The information processing apparatus according to claim 1, wherein the at least one processor is configured to determine, in a case in which there are a plurality of the existing sentences, the arrangement order for determining an insertion position of the new sentence while an arrangement order of the plurality of existing sentences is fixed.

5. The information processing apparatus according to claim 1, wherein:

the medical information indicates at least one of a type of an organ, a type of a lesion, or a type of an examination, and the at least one processor is configured to determine the arrangement order such that the existing sentence and the new sentence are arranged for each type of the medical information.

6. The information processing apparatus according to claim 1, wherein:

the medical information indicates a property of a lesion, and the at least one processor is configured to determine the arrangement order such that the existing sentence and the new sentence are arranged for each property of the medical information.

7. The information processing apparatus according to claim 1, wherein the at least one processor is configured to:

specify a factuality regarding the medical information from each of the existing sentence and the new sentence; and determine the arrangement order such that the existing sentence and the new sentence are arranged for each factuality regarding the medical information.

8. The information processing apparatus according to claim 1 wherein:

the medical information has a predetermined importance, and the at least one processor is configured to determine the arrangement order such that the existing sentence and the new sentence with a higher importance of the medical information are positioned closer to a beginning of a sentence.

9. The information processing apparatus according to claim 1, wherein:

the medical information indicates a point in time at which an examination is performed, and the at least one processor is configured to determine the arrangement order such that the existing sentence and the new sentence are arranged in chronological order.

10. The information processing apparatus according to claim 1, wherein the at least one processor is configured to:

acquire a past document including a sentence describing medical information of the subject; and determine the arrangement order based on whether or not the medical information corresponding to the existing sentence and the new sentence is included in the past document.

11. The information processing apparatus according to claim 1, wherein at least one of the existing sentence or the new sentence includes a sentence generated based on a medical image.

12. The information processing apparatus according to claim 1, wherein the at least one processor is configured to rearrange the existing sentence and the new sentence based on the determined arrangement order.

13. The information processing apparatus according to claim 12, wherein the at least one processor is configured to highlight the new sentence and display the existing sentence and the new sentence after the rearrangement on a display.

14. The information processing apparatus according to claim 12, wherein the at least one processor is configured to highlight, in a case in which the existing sentence is rearranged, the rearranged existing sentence and display the existing sentence and the new sentence after the rearrangement on a display.

15. The information processing apparatus according to claim 1, wherein the at least one processor is configured to display information indicating a rule for the arrangement order on a display.

16. A non-transitory computer-readable storage medium storing an information processing program for causing a computer to execute a process comprising:

inputting a region of interest included in a medical image to a trained model;

causing the trained model to output medical information indicating a name, a type, a property, a measured value, a position, and an estimated disease name including a negative or positive evaluation result, related to the region of interest;

generating a new sentence including a description based on the medical information;

acquiring at least one existing sentence and the new sentence described after the existing sentence, mutually different medical information of the same subject being described in the existing sentence and the new sentence;

specifying a word included in each of the existing sentence and the new sentence;

generating medical information data corresponding to the specified word, the medical information data representing medical information that is represented by or related to the specified word, and associating the generated medical information data with each of the existing sentence and the new sentence; and determining an arrangement order of the existing sentence and the new sentence in accordance with a predetermined rule based on the associated medical information data.

* * * * *